(12) United States Patent
Carrigan et al.

(10) Patent No.: US 6,576,116 B2
(45) Date of Patent: Jun. 10, 2003

(54) HYBRID JOULE HEATING/ELECTRO-OSMOSIS PROCESS FOR EXTRACTING CONTAMINANTS FROM SOIL LAYERS

(75) Inventors: Charles R. Carrigan, Tracy, CA (US); John J. Nitao, Castro Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/874,167

(22) Filed: Jun. 13, 1997

(65) Prior Publication Data

US 2003/0024815 A1 Feb. 6, 2003

(51) Int. Cl.$^7$ .................................................. C25C 1/22
(52) U.S. Cl. .................... 205/687; 205/766; 205/769; 204/515; 204/DIG. 8; 588/204
(58) Field of Search .................... 588/204; 205/688, 205/766, 769; 204/515, DIG. 8

(56) References Cited

U.S. PATENT DOCUMENTS

| | | | |
|---|---|---|---|
| 5,137,608 A | 8/1992 | Acar et al. | 204/130 |
| 5,330,291 A | 7/1994 | Heath et al. | 405/128 |
| 5,433,829 A * | 7/1995 | Pool | 204/515 |
| 5,738,778 A * | 4/1998 | Doring | 205/766 |

OTHER PUBLICATIONS

Carrigan et al., A fully Coupled Model for 3–D, partially saturated flow and Transport in Soil Ohmically heated by application of Multiphase A.C. Electrical potentials Apr. 1995.*

UCRL–JC–120954, "A Fully Coupled Model For 3–D, Partially Saturated Flow And Transport In Soil Ohmically Heated By Application Of Multiphase A.C. Electrical Potentials", C.R. Carrigan et al., Apr. 1995.

* cited by examiner

Primary Examiner—Arun S. Phasge
(74) Attorney, Agent, or Firm—L. E. Carnahan; Alan H. Thompson

(57) ABSTRACT

Joule (ohmic) heating and electro-osmosis are combined in a hybrid process for removal of both water-soluble contaminants and non-aqueous phase liquids from contaminated, low-permeability soil formations that are saturated. Central to this hybrid process is the partial desaturation of the formation or layer using electro-osmosis to remove a portion of the pore fluids by induction of a ground water flow to extraction wells. Joule heating is then performed on a partially desaturated formation. The joule heating and electro-osmosis operations can be carried out simultaneously or sequentially if the desaturation by electro-osmosis occurs initially. Joule heating of the desaturated formation results in a very effective transfer or partitioning of liquid state contaminants to the vapor phase. The heating also substantially increases the vapor phase pressure in the porous formation. As a result, the contaminant laden vapor phase is forced out into soil layers of a higher permeability where other conventional removal processes, such as steam stripping or ground water extraction can be used to capture the contaminants. This hybrid process is more energy efficient than joule heating or steam stripping for cleaning low permeability formations and can share electrodes to minimize facility costs.

20 Claims, 4 Drawing Sheets

HYBRID JOULE HEATING/ELECTRO-OSMOSIS PROCESS FOR EXTRACTING CONTAMINANTS FROM SOIL LAYERS

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to extracting contaminants from soil, particularly to extracting contaminants from low-permeability soil layers, and more particularly to a hybrid joule heating/electro-osmosis process for extracting water soluble and non-aqueous phase liquid contaminants from saturated, low-permeability soil layers.

Contaminants migrating from various types of facilities, accidental spills, and industrial operations threaten health and ground water supplies. Such contamination often covers large volumes of soil underlying several acres of surface area. In view of the high cost of land, limited resources, and the fact that contamination can occur in densely populated areas, such as from leakage of fuel or gas storage tanks or lines, or industrialized areas adjacent dense populated areas, there exists a need to find economical and efficient technologies of remediation for rapid reclamation and rehabilitation of such areas.

Many facilities have suffered contamination of the vadose and saturated regimes by the spilling, or leakage, for example, of dense non-aqueous phase liquids (DNAPLs), such as trichlorethylene (TCE) and other solvents to produce localized sources of contamination. Pump-and-treat methods applied to the source may only dilute the contamination but not remove or even reduce it. Soil removal may be impractical owing to the large volumes that have become contaminated at some sites. Techniques that remediate by either in situ contaminant mobilization and extraction or by in situ breakdown of the contamination into harmless products avoid some of the disadvantages that characterize the pump-and-treat or soil-removal schemes. Steam injection, extraction and air-sparging remediation processes already exist for in situ treatment of moderate-to-high permeability soils. However, the techniques are generally inappropriate for application to low permeability clay layers that have suffered contamination. Cleaning up the higher permeability layers of the soil while neglecting the contamination in adjacent lower permeability formations may permit federal water quality standards to be achieved for several years following cleanup. However, eventually the low permeability contaminated soils will provide a contamination source for the surrounding soil layers, as leaching occurs which results in a decrease of water quality with time.

A process involving ohmic or joule heating of low permeability soil by passing alternating electrical currents through the soil, as a means of in situ contamination mobilization has been studied in some detail (see R. Newmark, Dynamic Underground Stripping Project LLNL Gasoline Spill Demonstration Report 6, UCRL-ID-113521, 1994; and C. R. Carrigan et al., A Fully Coupled Model for 3-D, Partially Saturated Flow and Transport in Soil Ohmically Heated by Application of Multiphase A. C. Electrical Potentials, UCRL-JC-120954, 1996). In addition to mobilizing contamination, ohmic dissipation also provides a potential source of heat for destroying contaminants in situ by hydrous pyrolysis (see K. G. Knauss et al., TCE: Thermodynamic measurements and destruction via hydrous pyrolysis/oxidation, Geol. Soc. Am. Abstr., Vol. 27, No. 6, p. 249, 1995). Electrical heating as a means of either contaminant mobilization or destruction appears to offer significant advantages over steam heating when low permeability clay layers are present. The heating of such soil layers is accomplished by implanting two or more alternating current (AC) electrodes on the edge of the targeted zone of contamination. Two electrodes are the minimum number, but the heating distribution will have little uniformity between the two electrodes. Thus, heating arrangements have used six or more electrodes in a circle to produce more uniform heating of the targeted area. In addition phase-shifting the alternating current applied to each electrode (e.g., the current applied to each electrode of a six-electrode array would be electrically phase shifted by 60 degrees), enhances the heating uniformity of the target zone at the center of the circle (see U.S. Pat. No. 5,330,291 issued Jul. 19, 1994 to W. O. Heath et al., for example). Also, using a six-electrode array, the electrical connections can also involve a three-phase heating arrangement with the six electrodes grouped in three pairs. While the six phase arrangement produces the greatest initial uniform heating, the most serious heating uniformity issues arise when the heating electrodes have been in operation long enough (typically an hour to a day depending on the current applied) to dry out the low permeability soil immediately adjacent to the electrodes. This presents a very serious problem for the ohmic or joule heating technique since groundwater in the soil is a major determining factor of the electrical conductivity of the soil. Thus, drying out of the soil immediately around an electrode is comparable to losing that electrode from the heating circuit, whereby maintaining current carrying capability by resaturation of the soil around the electrodes is necessary.

Another and different electro-remediation phenomenon, known as electro-osmosis, which has been utilized for various applications for about five decades, has been recently considered by researchers as a means of transporting across a porous regime either contamination or solutions intended to mobilize contamination. (See A. P. Shapiro et al., Removal of Contaminant From Saturated Clay by Electro-osmosis, Environ. Sci. Technol., 27, 283–291, 1993; and R. F. Probstein et al., Removal of Contaminants From Soils by Electric Fields, Science, 260, 498–503, 1993.) In addition experiments have demonstrated the ability of electro-osmosis to remove soluble organics from clays. (See Y. B. Acar et al, Phenol Removal From Kaolinite by Electrokinetics, J. Geotech. Eng., 118, 1837–1852, 1992; and U.S. Pat. No. 5,137,608 issued Aug. 11, 1992 to Y. B. Acar et al.), Electro-osmosis is the flow of an ion-containing liquid with respect to a charged surface (i.e., porous medium) in response to an applied electric field across the porous medium. Several models exist that describe the dynamic relationship between the ions in the fluid and the applied field that results in the flow. However, the often-assumed Helmholtz-Smoluchowski Model (See A. T.

Young, Electro-kinetic Flow Processes in Porous Media and Their Applications (Chap. 5) in Advances in Porous Media (M. Y. Corapcioglu, ed. 2, Elsevier Amsterdam, pp. 309–395, 1994) provides the simplest and quantitatively adequate understanding of the process. The application of an electric field to a non uniformly distributed charge distribution in a fluid causes the fluid to be more or less dragged through to pore space. Clay pore walls tend to have a negative residual charge which produces the required non uniform charge distribution in the adjacent ion filled fluid. As a remedial technique, the phenomenon has significant potential for restoring low permeability, small-pore, contaminated soils (e.g., clays) since the induced flow does not depend strongly on pore size. On the other hand, for flow in a porous medium that is induced by a simple hydraulic head, there is a strong dependence on pore size with the flux being proportional to the cube of the effective pore diameter. Estimates (see A. P. Shapiro, et al., supra) indicate that electric field strengths of 100 V/m can give rise to electro-osmotic velocities (pore velocities) of about 10 cm/day on a saturated clay. Application of the electro-osmotic process is not new, as pointed out above, and has been applied successfully in civil engineering, separation science and physiological contexts. It has also been used on a large scale for the dewatering of saturated clays to provide a stable foundation for overlying structures. If transport in a low permeability contaminated layer is a necessary component of a remediation scheme, an electro-kinetic mechanism appears to be the only viable possibility.

The present invention involves hybrid processes or techniques for remediating contamination in tight (low permeability) soil layers. These techniques utilize a combination of ohmic or joule heating and electro-osmosis. One technique or process involves in situ destruction of the contamination, while the other involves driving the contamination from the soil layer. In the first hybrid process, electro-osmosis provides the means of transporting oxygen as part of an in situ contaminant destruction technique while electrical dissipation in the soils produces the heating to achieve favorable hydrous pyrolysis reaction rates. In this first hybrid process, a contaminant, such as TCE, is pyrolyzed or "burned" in a hydrous state by providing heat and dissolved oxygen at the same point. In the second hybrid process, described in detail hereinafter, which involves mobilization of the contaminant in the tight or low permeability layer, successful partial desaturation by electro-osmosis will permit the highly effective partitioning of volatile contaminants into the vapor phase which is far more mobile than the liquid phase of a free product or a dissolved contaminant. Heating the resulting partially saturated regime with the same electrodes can drive off the vapor to regions of higher permeability where air sparging or vacuum extraction can be applied. By combining electro-osmosis with ohmic heating, the problem associated with the inherent tendency of ohmic heating to dry the ground out around the electrode well is eliminated. Applying a direct current (dc) voltage difference between an alternating current (ac) ohmic heating electrode and a nearby "satellite" dc electrode will induce a groundwater flow toward the ac electrode that can offset the tendency for the ac electrode to dry out the soil thereabouts. The ohmic or joule heating and the electro-osmosis processes can be carried out simultaneously or can be carried out sequentially if the desaturation by electro-osmosis occurs initially.

SUMMARY OF THE INVENTION

It is an object of the present invention to provide a process for removing contaminants from saturated, low-permeability soil.

A further object of the invention is to provide a hybrid joule heating/electro-osmosis process for removing contaminants from the soil.

A further object of the invention is to provide for the destruction of contaminants in situ by providing oxygen and heat for hydrous pyrolysis to occur.

A further object of the invention is to provide a joule heating/electro-osmosis process for extracting water soluble and non aqueous phase liquid contaminants from saturated, low-permeability soil layers.

Another object of the invention is to combine joule (ohmic) heating and electro-osmosis processes, wherein partial desaturation of a soil formation or layer is carried out using electro-osmosis to remove a portion of the pore fluid by induction of a ground water flow to extraction wells, whereafter joule heating is performed on the partially desaturated formation.

Another object of the invention is to provide a soil contamination removal process which utilizes joule heating and electro-osmosis simultaneously or sequentially provided desaturation by electro-osmosis occurs initially.

Another object of the invention is to provide a combined joule (ohmic) heating/electro-osmosis process for removing contaminants from a saturated low-permeability soil, wherein transfer of liquid state contaminants to the vapor phase takes place and substantially increases the vapor phase pressure such that the contaminant laden vapor phase is forced out of the low-permeability soil layers into higher permeability soil where such can be removed by conventional processes.

Other objects and advantages of the present invention will become apparent from the following description and accompanying drawings. The invention broadly involves decontamination of soil by the use of a hybrid joule (ohmic) heating/electro-osmosis process. More specifically the invention involves a hybrid joule heating/electro-osmosis process for extracting both water-soluble contaminants and non-aqueous phase liquids (NAPLs) from contaminated, low-permeability soil formations that are saturated. Partial desaturation of the formation is carried out using electro-osmosis, followed by joule (ohmic) heating of the partially desaturated formation. Joule heating of the desaturated formation results in transfer or partitioning of liquid state contaminants to the vapor phase. The heating also substantially increases the vapor phase pressure, and thus the contaminant laden vapor phase is forced out into soil layers of higher permeability where it can be removed by stream stripping or ground water extraction, for example, to capture the contaminants. This hybrid process is more energy efficient than joule heating or steam stripping for cleaning low-permeability formations and the electro-osmosis process can share electrodes with the joule heating process to minimize facility costs. The invention can be effectively utilized, for example, to extract gasoline products or other volatile contaminants from clay layers.

BRIEF DESCRIPTION OF THE DRAWINGS

The accompanying drawings, which are incorporated into and form a part of the disclosure, illustrate methodology of the invention and, together with the description, serve to explain the principles of the invention.

DETAILED DESCRIPTION OF THE INVENTION

Figure 1:
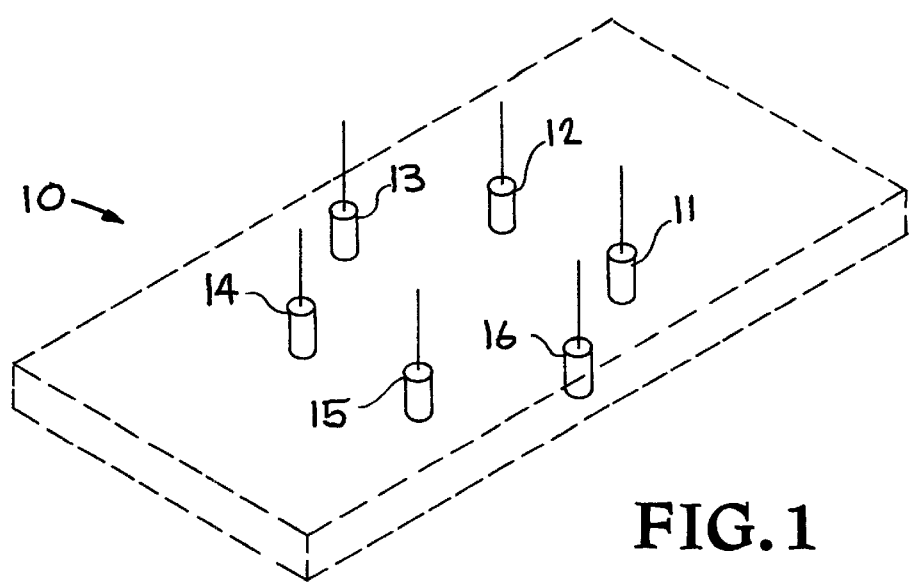
FIG. 1 schematically illustrates a conventional six heating electrode arrangement encircling a low-permeability target soil layer.

The present invention is directed to a process using joule (ohmic) heating and electro-osmosis for remediating contamination in tight (low-permeability) soil layers. The combined joule heating (JH)/electro-osmosis (EO) process enables at least two hybrid schemes for remediation of low-permeability soil contaminants: the first involves in situ destruction of the contamination; the second involves driving the contamination from the layer. In the first hybrid scheme, electro-osmosis provides the means for transporting oxygen as part of the in situ contaminant destruction scheme while electrical dissipation in the soil produces the heating to achieve favorable hydrous pyrolysis reaction rates, whereby a contaminant, such as trichloroethylene (TCE), is pyrolyzed or burned in a hydrous state by providing heat and dissolved oxygen at the same point. In the second hybrid scheme, the preferred scheme described hereinafter in detail and illustrated in the drawings, seeks mobilization of the contaminant in the tight (low-permeability) layer, and involves successful partial desaturation by electro-osmosis which permits a highly effective partitioning of volatile contaminants into a vapor phase which is far more mobile than the liquid phase of a free product or a dissolved contaminant. Heating the resulting partially saturated regime with the same electrodes drives of the vapor to regions of higher permeability soil, where air sparging or vacuum extraction to collect the contaminants can be applied.

The combining of electro-osmosis with joule heating, prevents or reduces the inherent tendency of joule heating to dry out the ground around the electrode wells, thus eliminating this widely recognized problem associated with joule heating. Applying a dc voltage difference between an ac joule (ohmic) heating electrode and a nearby "satellite" dc electrode will induce a groundwater flow toward the ac electrode that can, in principle, offset the tendency for the ac electrode to dry out. Experiments have shown that simply adding water to a heating electrode well did not resaturate dried out clay zones adjacent to an electrode. The main effect of adding water was that steam was produced within the electrode well and then driven into high permeability zones above the clay zone. The steam tends to heat the high permeability zone as well as condense within it. The result was that the electrical conductivity is increased wherever the steam goes, leading to greater current flow and joule (ohmic) dissipation in the high permeability zone instead of in the targeted low permeability clay zone.

While substantial efforts have been directed to electro-osmosis and to joule (ohmic) heating, in the context of environmental cleanup, joule heating and electro-osmosis have usually been viewed as competing methodologies for remediation. However, hybrid approaches combining aspects of both processes such as transport in low permeability media (electro-osmosis and local heating (joule or ohmic dissipation) represents a novel and unique class of remediation schemes or techniques that have the potential to overcome drawbacks of these separate methods.

Figure 2A:
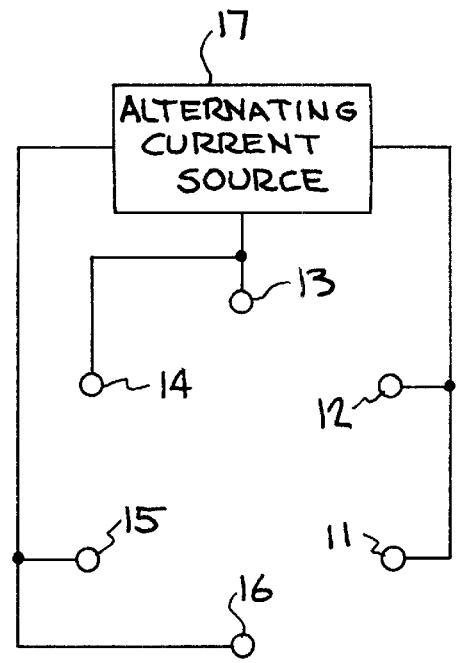
FIGS. 2A and 2B schematically illustrate three-phase and six-phase electrical connections for the six electrode arrangement of FIG. 1.
Figure 2B:
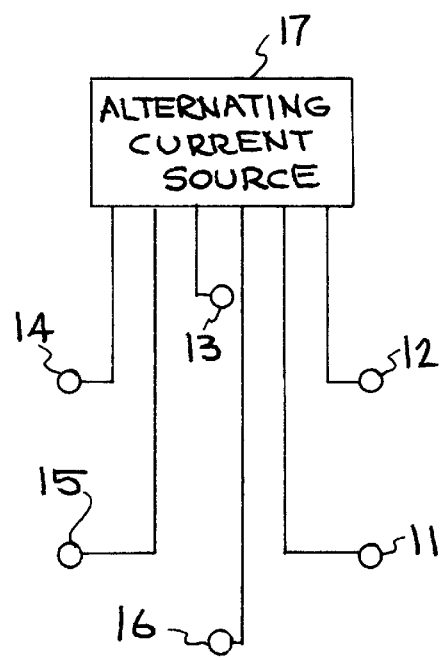

Referring now to the drawings, FIG. 1 illustrates a conventionally used six electrode joule heating arrangement in a low permeability target layer 10, with the electrodes being indicated at 11–16. The six electrodes 11–16 may be connected electrically to a alternating current (ac) source 17 in a three-phase arrangement, as shown in FIG. 2A or in a six-phase arrangement, as shown in FIG. 2B. Both the three-phase and the six-phase arrangements have been widely utilized in the joule heating (JH) process, and d.c. arrangements have been considered in the electro-osmosis (EO) process. If desired more or less than six joule heating electrodes may be used, as well as other phase arrangements. JH/EO electrodes (FIG. 4) involves both alternating and direct current. If desired direct current only could be utilized, electro-osmosis requires a direct current utilization.

Figure 3:
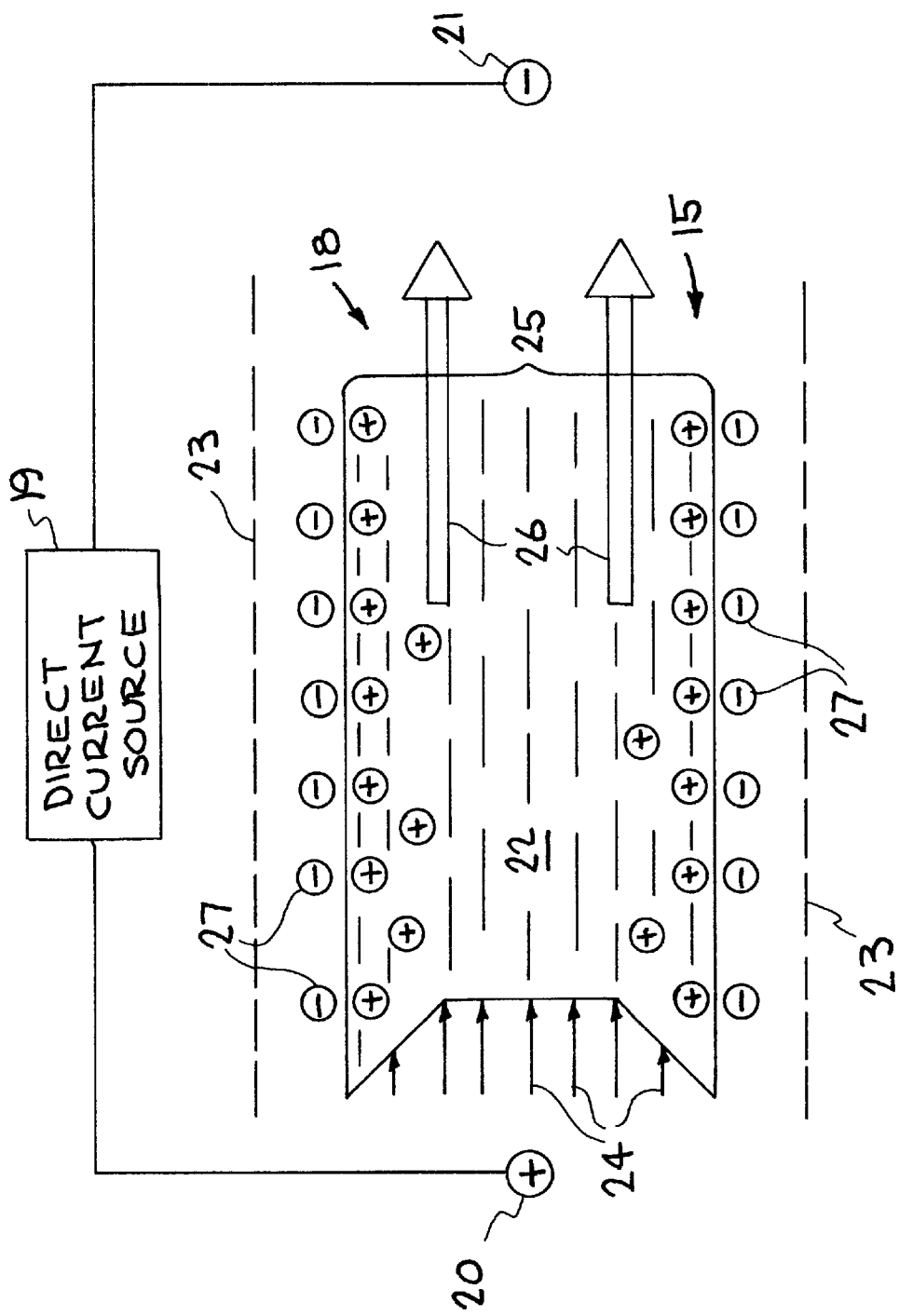
FIG. 3 schematically illustrates the Helmholtz-Smoluchowski model of the dynamic relationship between the ions in the fluid and the applied field that results in the flow.

As set forth above, electro-osmosis is the flow of an ion-containing liquid with respect to a charged surface (i.e., porous medium) in response to an electric field across the porous medium, and that several models exist that describe the dynamic relationship between the ions in the field and the applied field that results in the flow, with the Helmholtz-Smoluchowski model (see A. T. Young, supra) providing the simplest quantitatively adequate understanding of the process. As illustrated in FIG. 3, the application of an electric field 18, produced by a direct current (dc) source 19 connected to an anode 20 and cathode 21, to a non-uniformly distributed charge distribution in a fluid 22 causes the fluid 22 to be dragged through a pore space 23, as indicated by arrows 24, with the mobile cation shell being indicated 25 and the electrical force being indicated by arrows 26. Clay pore walls tend to have a negative residual charge, indicated at 27, which produces the required non-uniform charge distribution, illustrated by the random location of the positive charges in the electric field 18, in the adjacent ion filled fluid.

As also pointed out above, as a remedial technique the electro-osmosis phenomenon has significant potential for restoring low-permeability, small-pore, contaminated soils (e.g., clays) since the induced flow does not depend strongly on pore size. Thus, as shown in FIGS. 4 and 5, electro-osmosis (EO) when combined with ohmic or joule heating (JH) produces results which overcome the drawbacks of the separate methods.

Figure 5:
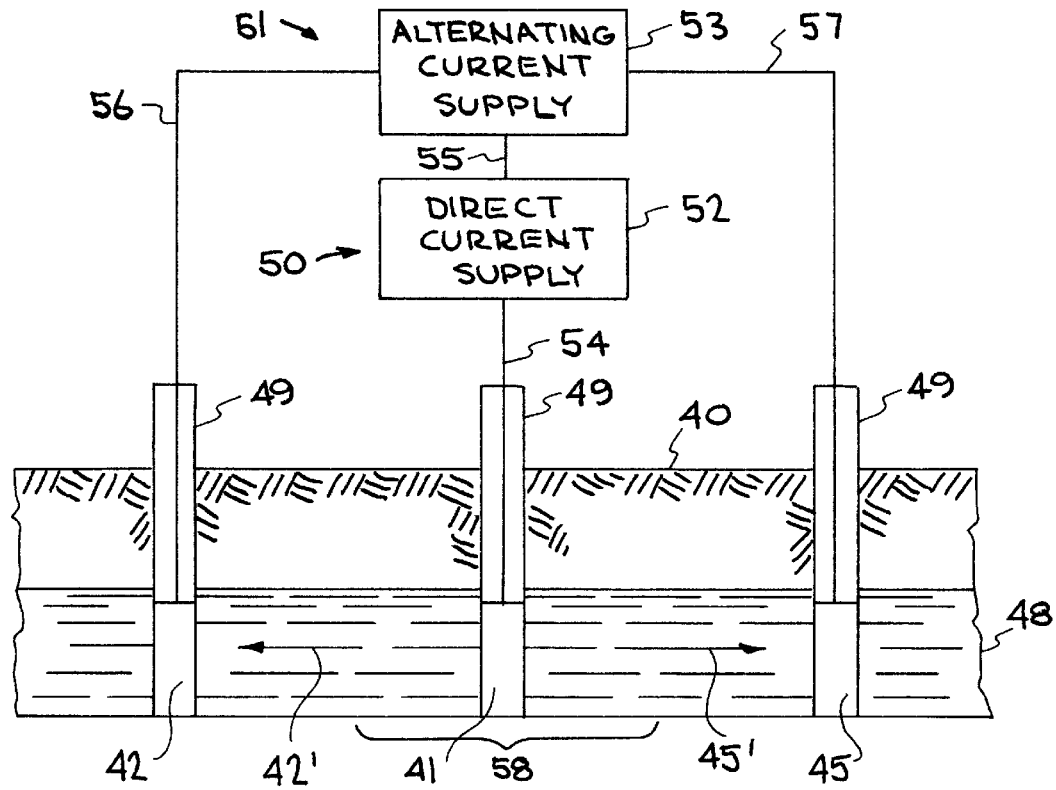
FIG. 5 is an enlarged cross-sectional view taken through three of the electrodes of the electrode array of FIG. 1, and schematically illustrating the electrical connections to the electrodes for both joule heating and electro-osmosis.
Figure 4:
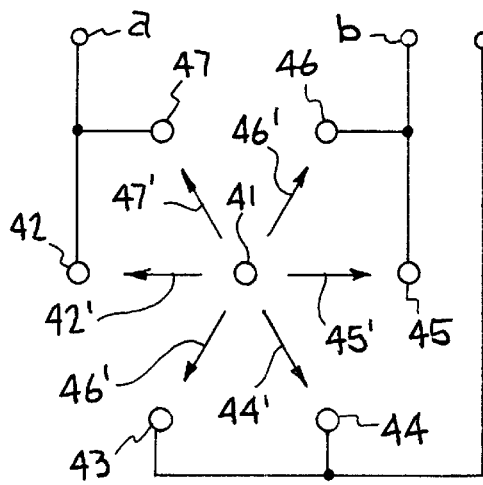
FIG. 4 is a top view of an electrode array positioned in a low-permeability soil layer for carrying out the joule heating/electro-osmosis (JH/EO) process of the present invention, and showing the induced electro-osmotic flow.

Referring now to FIGS. 4 and 5, FIG. 4 illustrates schematically a top view of an area 40 having a contaminated low-permeability target layer therebeneath as shown in cross-section in FIG. 5. The electrode embodiment illustrated in FIG. 4 comprises seven (7) porous electrodes with a center electrode 41 being an EO electrode and the surrounding six electrodes 42–47 being JH/EO electrodes. Arrows 42'–47' indicate induced electro-osmatic flow from EO electrode 41 to the JH/EO electrodes 42–47.

As shown in FIG. 5, the contaminated soil area 40 includes a low-permeability target layer 48 into which partially cased holes 49 are drilled and the electrodes 41–47 emplaced in the layer 48 with only EO electrode 41 and JH/EO electrodes 42 and 45 being illustrated in FIG. 5. It is to be understood that each of JH/EO electrodes 43, 44 and 46, 47 are similarly connected to EO electrode 41 or pairs of electrodes, such as 42, 47; 43, 44; and 45, 46 may be connected to EO electrode 41 to provide a six-phase (6 singles) or three-phase (3 pairs) arrangement; if desired. As shown in FIG. 5, both electro-osmosis, indicated at 50, and joule heating, indicated at 51, are carried out using the same electrodes via a dc power supply 52 and an ac power supply 53. The dc power supply 52 is connected to EO electrode 41 via lead 54 and by lead 55 to the ac power supply 53 and thus to JH/EO electrodes 42 and 45 via leads 56 and 57. Each JH/EO electrode is connected to both the dc and the ac power supplies 52 and 54. As the EO process proceeds the induced electro-osmotic fluid flow indicated arrows 42' and 45' create an expanding zone of desaturation indicated at 58 adjacent to EO electrode 41, which induced fluid flow prevents dry out of the soil around JH/EO electrodes 42 and 45.

Figure 6:
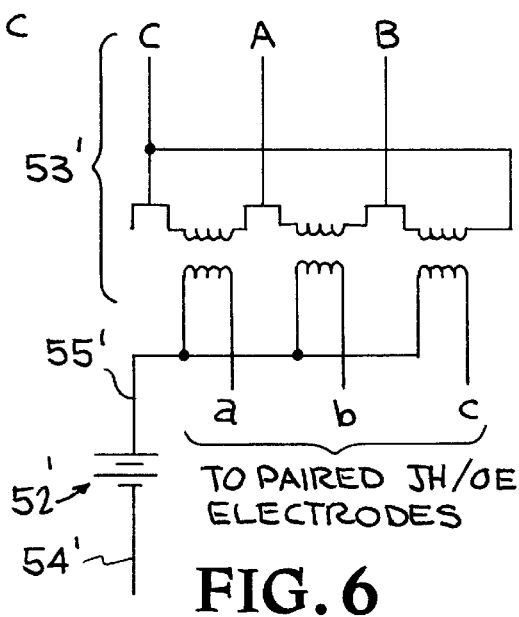
FIG. 6 is a schematic illustration of the ac power supply of FIG. 5.

FIG. 6 illustrates details of a conventional ac power supply 53' with connected dc supply 52' in accordance with FIGS. 4 and 5. FIG. 6 illustrates a standard 3 phase transformer delta-Y connection 53' connected to dc power supply 52' and via lead 54' to central EO electrode 41. In FIG. 6, A, B, and C are transformer primaries (from utility power) and a, b, and c of transformer 53' are transformer secondaries connected to pairs of interconnected JH/EO electrodes 42, 47; 43, 44' and 45 46, as indicated at a, b, and c in FIG. 4.

Figure 7:
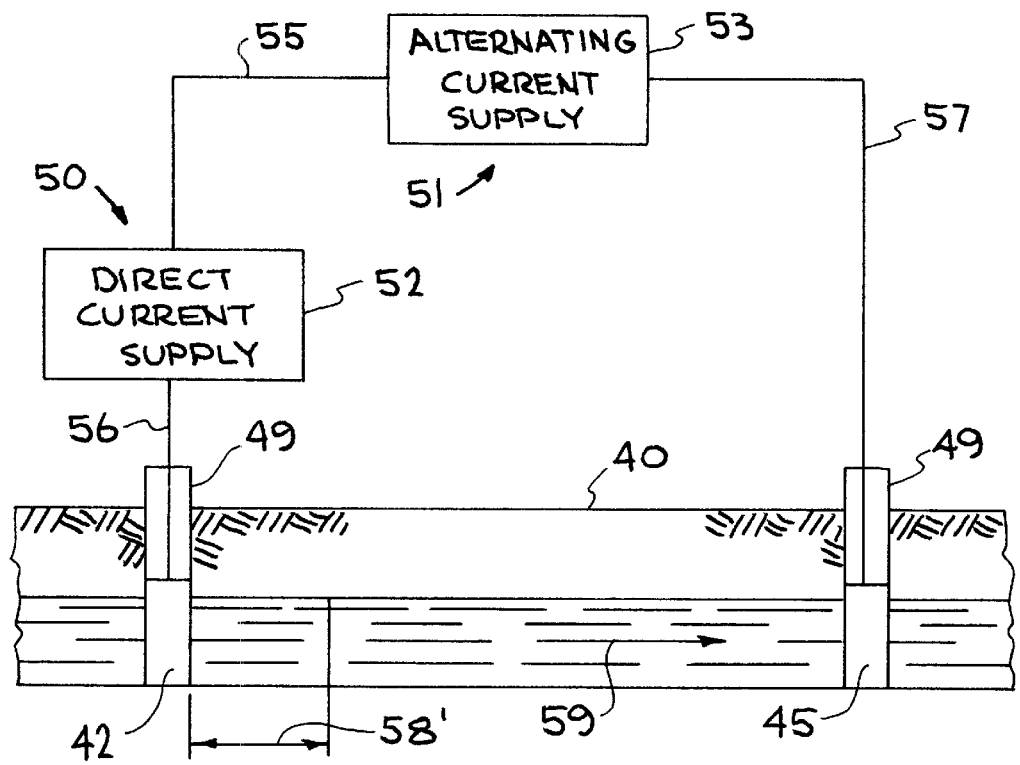
FIGS. 7 and 8 illustrate two-electrode embodiments of the invention.

FIG. 7 illustrates a two-electrode ac/dc joule heating/electro-osmosis arrangement. In this arrangement there are two porous JH/EO electrodes 42 and 45 connected to a dc power supply 52 and an ac power supply 53 to provide both joule heating 51 and electro-osmosis 50 at each electrode, whereby there is an induced fluid flow indicated by arrow 59 from electrode 42 toward electrode 45, resulting in an expanding zone of desaturation 58' adjacent electrode 42.

Figure 8:
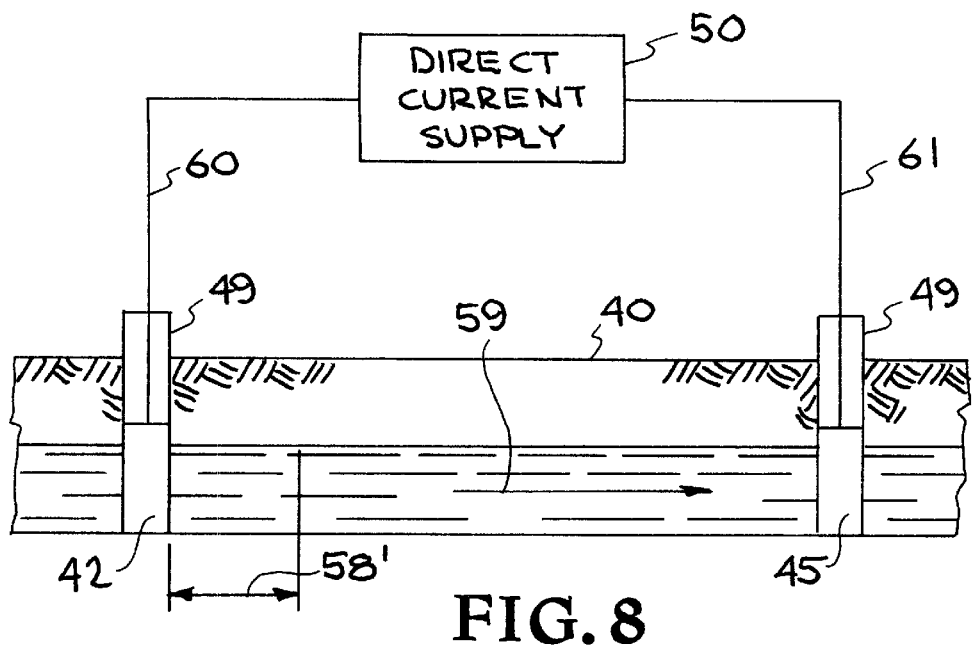

FIG. 8 is a two-electrode dc only joule heating/electro-osmosis arrangement. In this arrangement there are two porous JH/EO electrodes 42 and 45 connected to a dc power supply 50 by leads 60 and 61 to provide both joule heating and electro-osmosis at each electrode, whereby an induced fluid flow 59 is in the direction of electrode 45 producing an expanding zone of desaturation 58'. Here, there must be sufficient power in dc power supply 50 to produce joule heating, as well as electro-osmosis.

It has thus been shown that by using electro-osmosis partial desaturation of the pore fluid in the formation or layer around the EO electrode is removed by induction of ground water (fluid) flow to the extraction or JH/EO electrode wells. Joule heating is then performed on a partially desaturated formation to produce a contaminated vapor which can be captured by a conventional process. The joule heating and electro-osmosis processes can be carried out simultaneously or sequentially if the desaturation by electro-osmosis occurs initially. It has also been shown that the JH and EO processes can share electrodes to minimize facility costs.

While a particular embodiment of the invention has been illustrated and described to exemplify and explain the principles of the invention, such is not intended to be limiting. Modification and changes may become apparent to those skilled in the art, and it is intended that the invention be limited only by the scope of the appended claims.

The invention claimed is:

1. A process for removing contaminants from low-permeability soil, comprising:
   combining electro-osmoiss and joule heating to prevent dry out of soil adjacent to joule heating electrodes,
   said electro-osmosis and joule heating being carried out sequentially with electro-osmosis being carried out initially.

2. The process of claim 1, wherein electro-osmosis is utilized to partial desaturate the soil by removing a portion of the pore fluid in the soil by induction of a fluid flow to the joule heating electrode wells which also contributes to preventing dry out of the soil adjacent the joule heating electrode wells.

3. The process of claim 1, wherein joule heating is utilized to produce a contaminant laden vapor and force the vapor out of the low-permeability soil for capture thereof.

4. The process of claim 1, wherein electro-osmosis is carried out using an electro-osmosis electrode and a joule heating electrode.

5. The process of claim 1, wherein joule heating and electro-osmosis is carried out using at least one electro-osmosis electrode and a plurality of joule heating electrodes.

6. The process of claim 5, wherein the electrodes are electrically connected in a six-phase arrangement.

7. The process of claim 5, wherein the electrodes are electrically connected in a three-phase arrangement.

8. The process of claim 5, wherein the plurality joule heating electrodes are operatively connected to an alternating current power source and to a direct current power source, and wherein the at least one electro-osmosis electrode is operatively connected to a direct current power supply.

9. The process of claim 8, wherein the direct current power supply is operatively connected to the plurality of joule heating electrodes.

10. The process of claim 8, carried out by providing six joule heating electrodes and one electro-osmosis electrode, and operatively connecting the electro-osmosis electrode to each of the six joule heating electrodes.

11. The process of claim 1, wherein a plurality of electrodes are electrically connected to an alternating and direct current power supplies.

12. The process of claim 1, wherein a plurality of electrodes are electrically connected to only a direct current power supply.

13. A hybrid joule heating/electro-osmosis process for extracting water-soluble contaminants and non-aqueous phase liquids from saturated, contaminated, low-permeability soil formations, comprising:
   providing partial desaturation of the formation using electro-osmosis to remove to portion of the pore fluid of the formation by induction of a ground water flow to extraction wells,
   performing joule heating on a partially desaturated formation causing transfer or partitioning of liquid state contaminants to the vapor phase, and increasing the vapor phase pressure in the formation such that the contaminant lade vapor phase is forced out into soil of higher permeability where such can be captured,
   said electro-osmosis and joule heating being carried out sequentially such that electro-osmosis occurs initially.

14. The process of claim 13, additionally utilizing conventional removal processes to capture the contaminant laden vapor.

15. The process of claim 13, wherein the electro-osmosis and the joule heating is carried out using shared electrodes.

16. The process of claim 15, the electro-osmosis is carried out using a single electrode and the joule heating is carried out using a plurality of electrodes, said single electrode being operatively connected to said plurality of electrodes.

17. The process of claim 16, wherein the joule heating is carried out by connecting the plurality of electrodes to an alternating current source and to a direct current source, and connecting the single electrode to a direct current source.

18. The process of claim 13, wherein the joule heating is carried out using a plurality of spaced electrodes, and wherein the electro-osmosis is carried out using a single electrode, each of said electrodes being operatively connected to a power supply such that there is an induced electro-osmotic fluid flow from the single electrode to each of the plurality of spaced electrodes.

19. The process of claim 13, wherein joule heating and electro-osmosis are carried out using a plurality of electrodes, each electrode being electrically connected to both direct current and alternating current.

20. The process of claim 13, wherein a plurality of electrodes are used with each electrode being connected only to a direct current power source.

* * * * *